(12) United States Patent
Cavalcanti et al.

(10) Patent No.: US 7,538,059 B2
(45) Date of Patent: May 26, 2009

(54) REGENERATION OF MIXED METAL OXIDE CATALYSTS

(75) Inventors: Fernando Antonio Pessoa Cavalcanti, Lafayette Hill, PA (US); Scott Han, Lawrenceville, NJ (US); Peter David Klugherz, Huntingdon Valley, PA (US); Andrew Michael Lemonds, Blue Bell, PA (US); Daniel J. Martenak, Perkasie, PA (US); Elsie Mae Vickery, Jenkintown, PA (US); Donald Lee Zolotorofe, Ivyland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 394 days.

(21) Appl. No.: 11/650,909

(22) Filed: Jan. 8, 2007

(65) Prior Publication Data

US 2007/0179042 A1 Aug. 2, 2007

Related U.S. Application Data

(60) Provisional application No. 60/763,790, filed on Jan. 31, 2006.

(51) Int. Cl.
*B01J 38/12* (2006.01)

(52) U.S. Cl. .......................................... 502/38; 502/29
(58) Field of Classification Search .................. 502/38, 502/20, 29
See application file for complete search history.

(56) References Cited

U.S. PATENT DOCUMENTS

| 4,052,333 | A | 10/1977 | Lee |
| 2003/0187298 | A1 | 10/2003 | Borgmeier et al. |
| 2005/0277547 | A1 | 12/2005 | Gaffney et al. |

FOREIGN PATENT DOCUMENTS

| FR | 2 855 514 A1 | 5/2003 |
| WO | WO 2005/047224 | 3/2005 |
| WO | WO 2006/072682 | 7/2006 |

*Primary Examiner*—Edward M Johnson
(74) *Attorney, Agent, or Firm*—Marcella M. Bodner

(57) ABSTRACT

A mixed metal oxide, which may be an orthorhombic phase material, is regenerated, selectively enriched or selectively poisoned as a catalyst to reduce catalyst aging for the production of unsaturated carboxylic acids, or unsaturated nitrites, from alkanes, or mixtures of alkanes and alkenes, by contacting said mixed metal oxide with a an oxidizing gas such as oxygen, air, steam and combinations thereof is permitted to flow through the catalyst in a regenerator at a temperature of from 300° C. to 600° C. to form said regenerated catalyst.

8 Claims, No Drawings

REGENERATION OF MIXED METAL OXIDE CATALYSTS

CROSS REFERENCE TO RELATED PATENT APPLICATIONS

This is a non-provisional patent application of U.S. provisional patent application Ser. No. 60/763,790 filed Jan 31, 2006.

The present invention relates to a regenerated catalyst, an enriched catalyst and a selectively poisoned catalyst for the oxidation of alkanes, or a mixture of alkanes and alkenes, to their corresponding unsaturated carboxylic acids by vapor phase catalytic oxidation and, more particularly, to a method of regenerating the catalyst and to a process for the vapor phase catalytic oxidation of alkanes, or a mixture of alkanes and alkenes, to their corresponding unsaturated carboxylic acids using a regenerated catalyst. The present invention also relates to a process regenerating a catalyst, a process for selectively enriching a catalyst and a process for selectively poisoning a catalyst, all related to the vapor phase catalytic oxidation of alkanes, or a mixture of alkanes and alkenes, in the presence of ammonia, to their corresponding unsaturated nitrites using a catalyst prepared by the present method of making a regenerated catalyst.

Mixed metal oxide catalysts used in the partial oxidation of propane to acrylic acid or ammoxidation of propane to acrylonitrile require stable operation for favorable process use and economics. In addition to the intrinsic aging behavior of a catalyst under long-term processing, methods to restore catalyst activity and stability, typically called regeneration or rejuvenation, are employed as the catalyst reaches particular end-of-cycle performance levels.

U.S. patent appl. Publ. No. US20050277547 A1 discloses a method wherein a part of a mixed metal oxide catalyst is withdrawn from the reaction zone from time to time, then sent to an oxidation regenerator, regenerated and then returned to the reaction zone for reuse. As the regeneration method of the catalyst, the method comprises contacting an oxidative gas such as oxygen, air or nitrogen monoxide with the catalyst in the regenerator usually at a temperature of from 300° to 600° C. It is desirable to provide alternative regenerative methods for restoring catalytic performance, which are employed at any of the various points in an oxidation process using mixed metal oxide catalysts.

Thus, in a first aspect, the present invention provides a process for regenerating a mixed metal oxide catalyst, said process comprising:

(a) providing a mixed metal oxide having the empirical formula

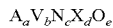

wherein A is at least one element selected from the group consisting of Mo and W, N is at least one element selected from the group consisting of Te and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, Sc, Cl, F and I,
wherein A, V, N and X are present in such amounts that the atomic ratio of A : V : N : X is a:b:c:d, and
wherein, when a =1, b =0.1 to 2, c=0.1 to 1, d=0.01 to 1 and e is dependent on the oxidation state of the other elements; and (b) contacting the mixed metal oxide catalyst at temperatures of from 300° to 600° C. with: oxidizing agents selected from the group consisting of: combustion gases, $NH_3$, $CO_2$, $H_2O$, a gaseous stream containing ozone, electrical polarization of the catalyst bed in an $O_2$-containing atmosphere, electrical current treatment of the catalyst bed, a gaseous stream of volatile organic peroxides and combinations thereof.

In a second aspect, the present invention provides improved catalysts produced by the process according to all aspects of the invention.

In a third aspect, the present invention provides a process for enriching a mixed metal oxide catalyst in element N comprising the steps of:

(a) providing an improved mixed metal oxide having the empirical formula

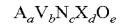

wherein A is at least one element selected from the group consisting of Mo and W, N is at least one element selected from the group consisting of Te, Se and Sb, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, Sc, Cl,
F
and I,
wherein A, V, N and X are present in such amounts that the atomic ratio of A : V : N : X is a :b :c : d, and
wherein, when a=1, b=0.1 to 2, c=0.1 to 1, d=0.01 to 1 and e is dependent on the oxidation state of the other elements; and (b) re-metallizing the mixed metal oxide catalyst by feeding a stream containing volatile organometallic compounds containing element N into the reactor or by removing and subjecting the mixed metal oxide catalyst to the chemical vapor deposition of element N.

In a fourth aspect, the present invention provides a process for extending the lifetime of a mixed metal oxide catalysts comprising the steps of:

(a) providing a mixed metal oxide having the empirical formula

wherein A is at least one element selected from the group consisting of Mo and W, N is at least one element selected from the group consisting of Te and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, Sc, Cl,
F
and I,
wherein A, V, N and X are present in such amounts that the atomic ratio of A : V : N : X is a:b:c:d, and
wherein, when a=1, b=0.1 to 2, c=0.1 to 1, d=0.01 to 1 and e is dependent on the oxidation state of the other elements; and (b) reversing flow direction of reactants in contact with the mixed metal oxide catalyst through the reactor.

The mixed metal oxide, which is used as the starting material for the present process of preparing a regenerated catalyst has the empirical formula

wherein A is at least one element selected from the group consisting of Mo and W, N is at least one element selected from the group consisting of Te and Se, and X is at least one element selected from the group consisting of Nb, Ta, Ti, Al, Zr, Cr, Mn, Fe, Ru, Co, Rh, Ni, Pt, Sb, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, Sc, Cl, F and I; and wherein, when a=1, b=0.01 to 2, c=0.01 to 1.0, d=0.01 to 0.1 and e is dependent on the oxidation state of the other elements.

Preferably, when a=1, b=0.1 to 0.5, c=0.05 to 0.5 and d=0.01 to 0.5. More preferably, when a=1, b=0.15 to 0.45, c=0.05 to 0.45 and d=0.01 to 0.1. The value of e, i.e. the amount of oxygen present, is dependent on the oxidation state of the other elements in the catalyst. However, e is typically in the range of from 3 to 4.7.

For example, such a mixed metal oxide may be prepared by:
  admixing compounds of elements A, V, N, X and at least one solvent to
  form a mixture,
    wherein A is at least one element selected from the group consisting of Mo and W, N is at least one element selected from
    the group consisting of Te and Se, and X is at least one element
    selected from the group consisting of Nb, Ta, Ti, Al, Zr, Cr, Mn,
    Fe, Ru, Co, Rh, Ni, Pt, Bi, B, In, Ce, As, Ge, Sn, Li, Na, K, Rb, Cs,
    Fr, Be, Mg, Ca, Sr, Ba, Hf, Pb, P, Pm, Eu, Gd, Dy, Ho, Er, Tm,
    Yb, Lu, Au, Ag, Re, Pr, Zn, Ga, Pd, Ir, Nd, Y, Sm, Tb, Br, Cu, Sc,
    Cl, F and I,
    wherein A, V, N and X are present in such amounts that the atomic
    ratio of A:V:N:X is a:b:c:d, and
    wherein, when a=1, b=0.01 to 2, c=0.01 to 1.0 and d=0.01 to 1.0;
  removing the at least one solvent from the mixture to form a precursor; and
  calcining the precursor to form a mixed metal oxide.

Preferred novel mixed metal oxides have the empirical formulae $Mo_aV_bTe_cNb_dO_e$ and $W_aV_bTe_cNb_dO_e$ wherein a, b, c, d and e are as previously defined.

Preferably, the mixed metal oxide to be used as the starting material is an orthorhombic phase material.

For example, the orthorhombic phase mixed metal oxide may be prepared by
  the process comprising:
    (a) providing a mixed metal oxide having the empirical formula

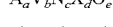

wherein A is at least one element selected from the group consisting of Mo and W, N is at least one element selected from the group consisting of Te and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, Sc, Cl, F and I,
    wherein A, V, N and X are present in such amounts that the atomic ratio of A : V :N : X is a:b:c:d, and
    wherein, when a=1, b=0.1 to 2, c=0.1 to 1, d=0.01 to 1 and e is dependent on the oxidation state of the other elements;
    (b) contacting said mixed metal oxide with a liquid contact member selected from the group consisting of organic acids, alcohols, inorganic acids and hydrogen peroxide to form a contact mixture; and
    (c) recovering insoluble material from said contact mixture to obtain said orthorhombic phase mixed metal oxide.

Alternatively, for example, such an orthorhombic phase mixed metal oxide may be prepared by a process comprising:
  (a) admixing compounds of elements A, V, N and X and at least one solvent to form a solution,
    wherein A is at least one element selected from the group consisting of Mo and W, N is at least one element selected from the group consisting of Te and
    Se, and X is at least one element selected from the group consisting of Nb, Ta,
    Ti, Al, Zr, Cr, Mn, Fe, Ru, Co, Rh, Ni, Pt, Bi, B, In, Ce, As, Ge, Sn, Li, Na, K,
    Rb, Cs, Fr, Be, Mg, Ca, Sr, Ba, Ra, Hf, Pb, P, Pm, Eu, Gd, Dy, Ho, Er, Tm,
    Yb, Lu, Au, Ag, Re, Pr, Zn, Ga, Pd, Ir, Nd, Y, Sm, Tb, Br, Cu, Sc, Cl, F and I,
    wherein A, V, N and X are present in such amounts that the atomic ratio of
    A:V:N:X is a:b:c:d, and
    wherein, when a=1, b=0.01 to 2, c=0.01 to 1.0 and d=0.01 to 1.0;
  (b) admixing a seeding effective amount of an orthorhombic phase mixed metal oxide seed, substantially free of hexagonal phase mixed metal oxide, with said solution to form a seeded solution;
  (c) removing said at least one solvent from said seeded solution to form a catalyst precursor; and
  (d) calcining said catalyst precursor to obtain said orthorhombic phase mixed metal oxide.

Suitable solvents, for the above-noted processes, include water; alcohols including, but not limited to, methanol, ethanol, propanol, and diols, etc.; as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, the amount of water is preferably sufficient to ensure an aqueous solution is formed.

The solvent is removed by any suitable method, known in the art, to form a catalyst precursor. Such methods include, without limitation, vacuum drying, freeze drying, spray drying, rotary evaporation and air drying.

For example, in the case of water being the solvent: Vacuum drying is generally performed at pressures ranging from 10 mmHg to 500 mmHg. Freeze drying typically entails freezing the solution, using, for instance, liquid nitrogen, and drying the frozen solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° to 90° C. and at a pressure of from 10 mmHg to 350 mmHg, more preferably at a bath temperature of from 40° C. to 60° C. and at a pressure of from 10 mmHg to 40 mmHg. Air drying may be effected at temperatures ranging from 25° C. to 90° C. Rotary evaporation or spray drying are generally preferred.

Contacting with a liquid contact member selected from the group consisting of organic acids, alcohols, inorganic acids and hydrogen peroxide (whether it be for the purpose of making the final catalyst, an orthorhombic phase mixed metal oxide, or for the purpose of making a seed material) may be effected without any particular restrictions (so long as, in the case of the preparation of the orthorhombic phase mixed metal oxide, the hexagonal phase is fully removed from the mixed metal oxide or the calcined precursor). The liquid contact member is normally used in an amount of 1 to 100 times the volume of the mixed metal oxide or the first calcined precursor, preferably 3 to 50 times the volume, more preferably 5 to 25 times the volume. (Contacting at elevated temperatures will remove the hexagonal phase more rapidly. However, if prolonged contact time is not a consideration, contacting at room temperature may be utilized.) Normally, contact temperatures of room temperature to 100° C. are utilized, preferably 50° C. to 90° C., more preferably 60° C. to 80° C. As previously noted, contact time will be affected by the temperature at which the contacting is carried out. Normally, contact times of 1 to 100 hours are utilized, preferably 2 to 20 hours, more preferably 5 to 10 hours. The contact mixture is preferably agitated during the contacting.

There are no particular restrictions upon the organic acids which may be used as the liquid contacting member. For example, oxalic acid, formic acid, acetic acid, citric acid and tartaric acid may be used, however, oxalic acid is preferred. If the organic acid is a liquid, it may be used as is or in an aqueous solution. If the organic acid is a solid, it is used in an aqueous solution. When using aqueous solutions, there are no particular restrictions on the concentration of the organic acid. Normally, the concentration of the organic acid in the aqueous solution can vary from 0.1 to 50% by weight, preferably 1 to 15% by weight.

There are no particular restrictions upon the alcohols which may be used as the liquid contacting member. For example, methanol, ethanol, propanol, butanol, hexanol and diols may be utilized, however, alcohols having one to four carbon atoms are preferred, with ethylene glycol being particularly preferred. The alcohols may be utilized in the form of aqueous solutions, but, if so, the water content should be held to 20% by weight or less for the best effectiveness.

Similarly, there are no particular restrictions upon the inorganic acids which may be used as the liquid contacting member. For example, telluric acid, nitric acid, sulfuric acid, phosphoric acid, hydrochloric acid, perchloric acid, chloric acid and hypochlorous acid may be used. The inorganic acids are typically used as aqueous solutions with concentrations of the acids in the range of from 0.1 to 50% by weight, preferably from 0.1 to 10% by weight.

When hydrogen peroxide is utilized as the liquid contacting member, it is used in the form of an aqueous solution having a concentration in the range of from 0.1 to 50% by weight, preferably from 1 to 10% by weight.

After contacting with the liquid contacting member, insoluble material is recovered from the so-formed contact mixture. The insoluble material may be recovered by any conventional method, e.g., centrifugation or filtration. If the contacting was conducted at elevated temperature, the contact mixture may be cooled prior to recovery of the insoluble material. If desired, the recovered insoluble material may be washed with one of the previously disclosed solvents, preferably water.

Calcination may be conducted in an oxidizing atmosphere, e.g., in air, oxygen-enriched air or oxygen, or in a non-oxidizing atmosphere, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired promoted mixed metal oxide.

In a preferred mode of operation, the catalyst precursor is calcined in two stages. In the first stage, the catalyst precursor is calcined in an oxidizing environment (e.g. air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 750° C., preferably for from 550° C. to 650° C., for 15 minutes to 8 hours, preferably for from 1 to 3 hours. Optionally, a reducing gas, such as, for example, ammonia or hydrogen, may be added during the second stage calcination.

According to one embodiment, the mixed metal oxide is regenerated using one or more oxidizing agents. Suitable oxidizing agents include, bur are not limited to for example combustion gases, $NH_3$, $CO_2$, $H_2O$, a gaseous stream containing ozone, electrical polarization of the catalyst bed in an $O_2$-containing atmosphere, electrical current treatment of the catalyst bed, a gaseous stream of volatile organic peroxides and combinations thereof.

According to one embodiment of the invention, the general order for making a regenerated catalyst includes 1) synthesizing the fresh catalyst, 2) employing (also referred to as aging) the catalyst in its application, e.g., propane oxidation, and 3) performing a regeneration process on the catalyst thereby making a regenerated catalyst.

According to a separate embodiment of the invention, the mixed metal oxide catalyst is treated in the reactor with a mixture of steam, air and ammonia at a temperature of from 200° C. to 800° C. Subjecting the catalyst to such an in-situ treatment in the reactor provided improvements in alkane oxidation performance for deactivated catalysts. The process is referred to as selectively poisoning the catalyst.

According to a separate embodiment of the invention, steam/air mixtures at elevated temperatures was used to regenerate/activate spent (also referred to as deactivated) or fresh mixed metal oxide catalysts for selective oxidation of propane to acrylic acid. Specifically, a Mo/V/Te/Nb oxide catalyst which was significantly deactivated by exposure to a strong reducing atmosphere was activated by contacting the catalyst with steam and air in a separate step but in-situ in the reactor.

According to one embodiment of the invention, the mixed metal oxide catalysts are regenerated using a re-metallizing method. Catalysts that deactivate due to the loss of one or more chemical constituents from the catalyst's surface are regenerated. Re-metallizing the mixed metal oxide catalyst is accomplished by feeding a stream containing volatile organometallic compounds containing element N into the reactor or by removing and subjecting the mixed metal oxide catalyst to the chemical vapor deposition of element N. Mixed metal oxide catalysts are re-metallized using any conventional technique, including but not limited to CVD, physical vapor deposition (PVD), metal sputtering and any other suitable deposition technique. Chemical vapor deposition (CVD) is used to replace these constituents in order to restore performance. CVD is well suited to regenerate deactivated catalysts used in gas-phase reactions because CVD is conducted in the gas phase; catalysts can thus be regenerated within the reactor for their catalytic application. Operational and economic advantages are presented because unpacking and replacement of the catalyst are not needed. Also, cycle time required to regain reactor performance is minimized. CVD processes require only hours to complete versus the weeks typically required to empty and reload a reactor with fresh catalyst. The catalyst may otherwise be removed from the reactor and subjected to CVD separately.

The loss of volatile metals, such as Te, from the mixed metal oxide catalyst surface during long-term operation may be remedied by subjecting the catalyst to CVD as described above. Organometallic CVD precursors are preferred for this application, as opposed to inorganics, because chemistries of the latter typically involve halides. Metal oxide CVD using halides produces byproducts detrimental to the catalyst, e.g., hydrogen halides. Furthermore, deposition temperatures required to minimize impurities from the precursor ligands are typically lower when organometallics are used.

According to another embodiment of the invention, regeneration is performed for mixed metal oxide catalyst beds that deactivate in a gradient-wise fashion, i.e., for beds that do not deactivate uniformly. Catalyst in the front of the reactor becomes heavily deactivated, since the extent of reaction in a plug-flow reactor increases the fastest in the front of the bed. Catalyst in the back is deactivated to a lesser degree, however, and bears utility for continued operation. For these reasons, it is advantageous to periodically reverse the flow of reactants through the reactor to prevent or slow the formation of heavily deactivated regions of the MMO catalyst. Flow switching allows the operator to more evenly distribute the degree of catalyst deactivation and extend the useful life of the catalyst charge.

The method may also regenerate MMO catalysts based upon the phenomenon of surface Te loss, which correlates with the deactivation of these catalysts. Desorbed Te can re-adsorb downstream onto cooler portions of the catalyst and the reactor walls. Flow switching enables the redistribution of Te throughout the bed and in turn regenerates the catalyst.

According to another embodiment of the invention, it was found that the MMO catalyst performance is improved with a sub-monolayer deposition of Te onto its surface by vapor deposition. The selectivity to acrylic acid improved by approximately 6% and the acrylic acid yield by 3%, absolute. Applying a similar Te loading onto MMO by wet impregnation methods did not improve catalytic performance. Post treatment of the Te vapor deposited MMO catalyst with oxygen at elevated temperatures gave improved catalytic performance when compared to a corresponding sample treated with an inert gas at the same elevated temperatures.

Further improvements in catalyst performance are anticipated with the optimization of the Te vapor deposition loading level on the mixed metal oxide surface, optimization of the oxygen thermal post treatment, evaluation of other metals (and related compounds) and combination of metals (and related compounds) added by vapor deposition to mixed metal oxide surfaces, including an optimized oxygen thermal post treatment.

Vapor deposition onto the mixed metal oxide catalyst surface may serve as a means of improving the performance of an on-stream catalyst that may have undergone performance degradation.

Vapor deposition may be accomplished by techniques known in the art, including physical vapor deposition, chemical vapor deposition, sputtering, anodic or cathodic arc deposition, thermal or plasma-supported gas phase deposition, and the like.

Regarding the conversion of propane to acrylic acid, synthesis of a mixed metal oxides with catalytic performances that match or out perform catalysts with compositions falling within the claims in the patent art may be realized by vapor deposition. For example, one may propose that a Mo—V-Ox mixed metal oxide may be synthesized by conventional methods (e.g., hydrothermal, spray dry, evaporative methods, etc.) and then treated by vapor deposition to provide monolayer coverage of Te and Nb so that the bulk compositional levels fall far below the patent claims of MMO. Assuming that the catalyst performance is largely based upon its surface chemistry, the hypothesis is that competitive acrylic acid yields may be realized with catalysts prepared by these methods.

In the production of an unsaturated carboxylic acid, it is preferred to employ a feed gas containing steam. In this case, a feed gas comprising the alkane or alkene raw material, steam, oxygen or an oxygen-containing gas is used. The steam may be introduced as a mixture with the alkane or alkane/alkene mixture which is delivered separately from the oxygen or oxygen-containing gas. The steam to be employed may be present in the form of steam gas in the reaction system, and the manner of its introduction is not particularly limited.

Further, as a diluting gas, an inert gas such as nitrogen, argon or helium may be supplied. The molar ratio (alkane or mixture of alkane and alkene): (oxygen): (diluting gas): ($H_2O$) in the starting material gas is preferably (1):(0.1 to 10):(0 to 20):(0.2 to 70), more preferably (1):(1 to 5.0):(0 to 10):(5 to 40)

When steam is supplied together with the alkane, or the mixture of alkane and alkene, as starting material gas, the selectivity for an unsaturated carboxylic acid is distinctly improved, and the unsaturated carboxylic acid can be obtained from the alkane, or mixture of alkane and alkene, in good yield simply by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with the steam.

As the starting material alkane it is preferred to employ a $C_{3-8}$ alkane, particularly propane, isobutane or n-butane; more preferably, propane or isobutane; most preferably, propane. According to the present invention, from such an alkane, an unsaturated carboxylic acid such as an α,β-unsaturated carboxylic acid can be obtained in good yield. For example, when propane or isobutane is used as the starting material alkane, acrylic acid or methacrylic acid will be obtained, respectively, in good yield.

In the present invention, as the starting material mixture of alkane and alkene, it is possible to employ a mixture of $C_{3-8}$ alkane and $C_{3-8}$ alkene, particularly propane and propene, isobutane and isobutene or n-butane and n-butene. As the starting material mixture of alkane and alkene, propane and propene or isobutane and isobutene are more preferred. Most preferred is a mixture of propane and propene. According to the present invention, from such a mixture of an alkane and an alkene, an unsaturated carboxylic acid such as an α,β-unsaturated carboxylic acid can be obtained in good yield. For example, when propane and propene or isobutane and isobutene are used as the starting material mixture of alkane and alkene, acrylic acid or methacrylic acid will be obtained, respectively, in good yield. Preferably, in the mixture of alkane and alkene, the alkene is present in an amount of at least 0.5% by weight, more preferably at least 1.0% by weight to 95% by weight; most preferably, 3% by weight to 90% by weight.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 700° C., but is usually in the range of from 200° C. to 550° C., more preferably 250° C. to 480° C., most preferably 300° C. to 400° C.; the gas space velocity, SV, in the vapor phase reaction is usually within a range of from 100 to 10,000 $hr^{-1}$, preferably 300 to 6,000 $hr^{-1}$, more preferably 300 to 2,000 $hr^{-1}$; the average contact time with the catalyst can be from 0.01 to 10 seconds or more, but is usually in the range of from 0.1 to 10 seconds, preferably from 2 to 6 seconds; the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

In the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem which enables the attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the promoted mixed metal oxide-containing catalyst of the present invention or by subjecting it to a vapor phase catalytic oxidation reaction with a conventional oxidation reaction catalyst for an unsaturated aldehyde.

The present invention provides a process for producing an unsaturated nitrile, which comprises subjecting an alkane, or a mixture of an alkane and an alkene, to a vapor phase catalytic oxidation reaction with ammonia in the presence of a catalyst produced in accord with the present invention to produce an unsaturated nitrile.

In the production of such an unsaturated nitrile, as the starting material alkane, it is preferred to employ a $C_{3-8}$ alkane such as propane, butane, isobutane, pentane, hexane and heptane. However, in view of the industrial application of nitriles to be produced, it is preferred to employ a lower alkane having 3 or 4 carbon atoms, particularly propane and isobutane.

Similarly, as the starting material mixture of alkane and alkene, it is possible to employ a mixture of $C_{3-8}$ alkane and $C_{3-8}$ alkane such as propane and propene, butane and butene, isobutane and isobutene, pentane and pentene, hexane and hexene, and heptane and heptene. However, in view of the industrial application of nitriles to be produced, it is more preferred to employ a mixture of a lower alkane having 3 or 4 carbon atoms and a lower alkene having 3 or 4 carbon atoms, particularly propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the ammoxidation reaction of this aspect of the present invention is not clearly understood. However, the oxidation reaction is conducted by the oxygen atoms present in the above promoted mixed metal oxide or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising an alkane, or a mixture of an alkane and an alkene, ammonia and an oxygen-containing gas, However, a gas mixture comprising an alkane or a mixture of an alkane and an alkene and ammonia, and an oxygen-containing gas may be supplied alternately.

When the gas phase catalytic reaction is conducted using an alkane, or a mixture of an alkane and an alkene, and ammonia substantially free from molecular oxygen, as the feed gas, it is advisable to employ a method wherein a part of the catalyst is periodically withdrawn and sent to an oxidation regenerator for regeneration by the method described in the first embodiment of this invention, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

The present invention will be described in further detail with respect to a case where propane is used as the starting material alkane and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the conditions for propane.

The process of this fourth aspect of the present invention may be conducted at a temperature of, for example, from 250° C. to 500° C. More preferably, the temperature is from 300° C. to 460° C. The gas space velocity, SV, in the gas phase reaction is usually within the range of from 100 to 10,000 $hr^{-1}$, preferably from 300 to 6,000 $hr^{-1}$, more preferably from 300 to 2,000 $hr^{-1}$. As a diluent gas, for adjusting the space velocity and the oxygen partial pressure, an inert gas such as nitrogen, argon or helium can be employed. When ammoxidation of propane is conducted by the method of the present invention, in addition to acrylonitrile, carbon monoxide, carbon dioxide, acetonitrile, hydrocyanic acid and acrolein may form as by-products.

EXAMPLES

Example 1

Selective propane oxidation to acrylic acid is carried out in a reactor containing a MoVTeNb oxide catalyst at 350° C. using a 3 s residence time (based on total feed gas flow rate) and a feed containing 7% propane, 14% $O_2$, 22%, and 57% $N_2$. After the catalyst activity decays such that the reactor operating temperature is increased to 390° C. in order to maintain productivity, the reactor is shut down and purged with inerts to remove all reaction products. Gas feed lines to the reactor are then valved to accommodate Te chemical vapor deposition precursor gas, composed mostly of an inert and a small percentage of the growth precursors, i.e., Te ethoxide ($Te(OCH_2CH_3)_4$) and optionally $H_2O$. The reactor outlet is switched over to a separate exhaust line, through which the reactor is subjected to vacuum. The reactor is pre-heated and evacuated. An inert gas is swept through the reactor, and the desired deposition temperature and pressure are allowed to stabilize. Precursor gas is then fed in place of the inert to perform the deposition. Required post-treatments (annealing, oxidation, etc.) are performed. Once the process is complete, the reactor is purged or treated to remove any unreacted precursor or byproducts. The reactor system is reconfigured for standard operation. This procedure can also be adapted for catalysts that lose more than one component. Compounds enabling the deposition of other transition metal oxides, such as Mo, are also available, and a combination can be used for multi-component CVD. Alternatively, other methods for metal deposition such as atomic layer deposition (ALD) maybe used using the procedure described above.

Example 2

A Pd/nitric acid Mo/V/Te/Nb oxide catalyst was prepared as described previously and extracted with oxalic acid. The catalyst was charged to a reactor and run for propane oxidation to acrylic acid under standard conditions. After the base catalyst performance was measured, air from the feed was shut off and reactor set point temperature was raised to 380° C. The catalyst was subjected to this reducing atmosphere for 8 hrs after which air was restored to the system and propane oxidation data taken. This procedure (air removal) was then repeated a second time to further deactivate the catalyst. After measuring propane-to-AA performance of the twice-deactivated catalyst, propane was removed from the feed such and reactor temperature raised to 380° C. again for 8 hrs. After this treatment, propane was restored and catalyst performance measured.

The data obtained are given in Table 1. The data indicate that the catalyst was deactivated significantly (from 54.5% to 23.6% AA yield) after treatment in a propane-only reducing atmosphere. However, a one-time treatment of the deactivated catalyst with the steam/air mixture raised both activity and selectivity of this catalyst for propane oxidation to acrylic acid.

TABLE 1

Catalytic performance of Pd/nitric acid/extracted Mo/V/Te/Nb oxide catalyst after propane-steam and air-steam treatments.
Pd/Nitric Acid Mo/V/Te/Nb Oxide Catalyst (Extracted With Oxalic Acid)
Feed = 3.9% $C_3H_8$/10% $O_2$/0% $H_2O$, Residence time = 3 sec.

| | | | | | |
|---|---|---|---|---|---|
| Feed Propane, % | 7.1 | 7.1 | 7.1 | 7.1 | 7.1 |
| Feed $O_2$, % | 14.9 | 14.9 | 15.0 | 15.0 | 14.9 |
| Feed Steam, % | 21.6 | 21.6 | 21.3 | 21.5 | 21.7 |
| Residence Time, sec. | 3.1 | 3.1 | 3.1 | 3.1 | 3.0 |
| Reactor Temp., ° C. | 323 | 350 | 362 | 345 | 348 |
| Peak Temp., ° C. | 374 | 404 | 408 | 372 | 392 |
| Exotherm, ° C. | 51 REMOVE AIR | 54 REMOVE AIR | 46 REMOVE PROPANE | 27 | 44 |
| Propane Conversion, mol % | 81.0 | 71.7 | 66.1 | 61 | 68 |
| $O_2$ Conversion, mol % | 94.0 PROPANE ONLY 380° C. | 99.6 PROPANE ONLY 380° C. | 99.6 STEAM + AIR ONLY 380° C. | 76 | 90 |
| Yields, mol % | | | | | |
| Propylene | 0.5 8 Hrs | 2.4 8 Hrs | 2.6 8 Hrs | 1.9 | 1.75 |

TABLE 1-continued

Catalytic performance of Pd/nitric acid/extracted Mo/V/Te/Nb oxide catalyst
after propane-steam and air-steam treatments.
Pd/Nitric Acid Mo/V/Te/Nb Oxide Catalyst (Extracted With Oxalic Acid)
Feed = 3.9% $C_3H_8$/10% $O_2$/0% $H_2O$, Residence time = 3 sec.

| | | | | | |
|---|---|---|---|---|---|
| $CO_2$ | 10.0 | 17.4 | 17.6 | 9.1 | 12.49 |
| CO | 10.4 | 16.7 | 16.5 | 10.9 | 14.38 |
| Acetone | 0.2 | 0.1 | 0.1 | 0.1 | 0.13 |
| Acetic Acid (HAc) | 5.6 | 4.9 | 4.5 | 3.7 | 3.85 |
| Propionic Acid | 0.4 | 0.3 | 0.3 | 0.2 | 0.14 |
| Acrylic Acid (AA) | 54.5 | 30.3 | 23.6 | 34.8 | 35.43 |
| AA Selectivity, mol % | 67.3 | 42.2 | 35.7 | 57.2 | 52.3 |

What is claimed is:

1. A process for regenerating a mixed metal oxide catalyst, said process comprising the steps of:
   (a) providing a mixed metal oxide having the empirical formula $$A_aV_bN_cX_dO_e$$

wherein A is at least one element selected from the group consisting of Mo and W, N is at least one element selected from the group consisting of Te and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, Sc, Cl, F and I,
   wherein A, V, N and X are present in such amounts that the atomic ratio of A:V:N:X is a:b:c:d, and
   wherein, when a=1, b=0.1 to 2, c=0.1 to 1, d=0.01 to 1 and e is dependent on the oxidation state of the other elements; and
   (b) contacting the mixed metal oxide catalyst at temperatures of from 300° to 600° C. with oxidizing agents selected from the group consisting of: combustion gases, $NH_3$, $CO_2$, $H_2O$, a gaseous stream containing ozone, electrical polarization of catalyst bed in an $O_2$-containing atmosphere, electrical current treatment of the catalyst bed, and a gaseous stream of volatile organic peroxides and combinations thereof.

2. The process for preparing a regenerated catalyst according to claim 1, wherein the mixed metal oxide of (a) is an orthorhombic phase mixed metal oxide.

3. An improved mixed metal oxide catalyst produced by the process according to claim 1.

4. A process for enriching a mixed metal oxide catalyst, said process comprising the steps of:
   (a) providing a mixed metal oxide having the empirical formula $$A_aV_bN_cX_dO_e$$

wherein A is at least one element selected from the group consisting of Mo and W, N is at least one element selected from the group consisting of Te and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, Sc, Cl, F and I,
   wherein A, V, N and X are present in such amounts that the atomic ratio of A:V:N:X is a:b:c:d, and
   wherein, when a=1, b=0.1 to 2, c=0.1 to 1, d=0.01 to 1 and e is dependent on the oxidation state of the other elements; and
   (b) re-metallizing the mixed metal oxide catalyst by feeding a stream containing volatile organometallic compounds containing element N.

5. The process for preparing an enriched catalyst according to claim 4, wherein the mixed metal oxide catalyst is re-metallized by subjecting the mixed metal oxide catalyst to chemical vapor deposition of element N.

6. A mixed metal oxide catalyst selectively enriched in element N produced by the process according to claim 4.

7. A process for extending the lifetime of a mixed metal oxide catalyst, said process comprising the steps of:
   (a) providing a mixed metal oxide having the empirical formula $$A_aV_bN_cX_dO_e$$

wherein A is at least one element selected from the group consisting of Mo and W, N is at least one element selected from the group consisting of Te and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, Sc, Cl, F and I,
   wherein A, V, N and X are present in such amounts that the atomic ratio of A:V:N:X is a:b:c:d, and
   wherein, when a=1, b=0.1 to 2, c=0.1 to 1, d=0.01 to 1 and e is dependent on the oxidation state of the other elements; and
   (b) reversing flow direction of reactants in contact with the mixed metal oxide catalyst through the reactor.

8. The process according to claim 7 wherein the flow direction is reversed periodically.

* * * * *